United States Patent [19]

Klaue

[11] Patent Number: 4,705,027
[45] Date of Patent: Nov. 10, 1987

[54] INTRAMEDULLARY NAIL

[75] Inventor: Kaj Klaue, Bern, Switzerland

[73] Assignee: Synthes Ltd. (U.S.A.), Paoli, Pa.

[21] Appl. No.: 733,930

[22] Filed: May 14, 1985

[30] Foreign Application Priority Data

May 14, 1984 [CH] Switzerland ..................... 2385/84

[51] Int. Cl.⁴ .............................................. A61F 5/04
[52] U.S. Cl. ........................... 128/92 YY; 128/92 VD
[58] Field of Search ........ 128/92 YY, 92 YZ, 92 YK, 128/92 Y

[56] References Cited

U.S. PATENT DOCUMENTS

| 4,281,649 | 8/1981 | Derweduwen | 128/92 YY |
| 4,475,545 | 10/1984 | Ender | 128/92 YY |
| 4,574,795 | 3/1986 | Georges | 128/92 YY |

Primary Examiner—C. Fred Rosenbaum
Assistant Examiner—C. W. Shedd
Attorney, Agent, or Firm—Davis Hoxie Faithfull & Hapgood

[57] ABSTRACT

An intramedullary nail has a tip portion provided with means for engaging a bolt previously inserted into a bone transverse to the bone axis.

12 Claims, 29 Drawing Figures

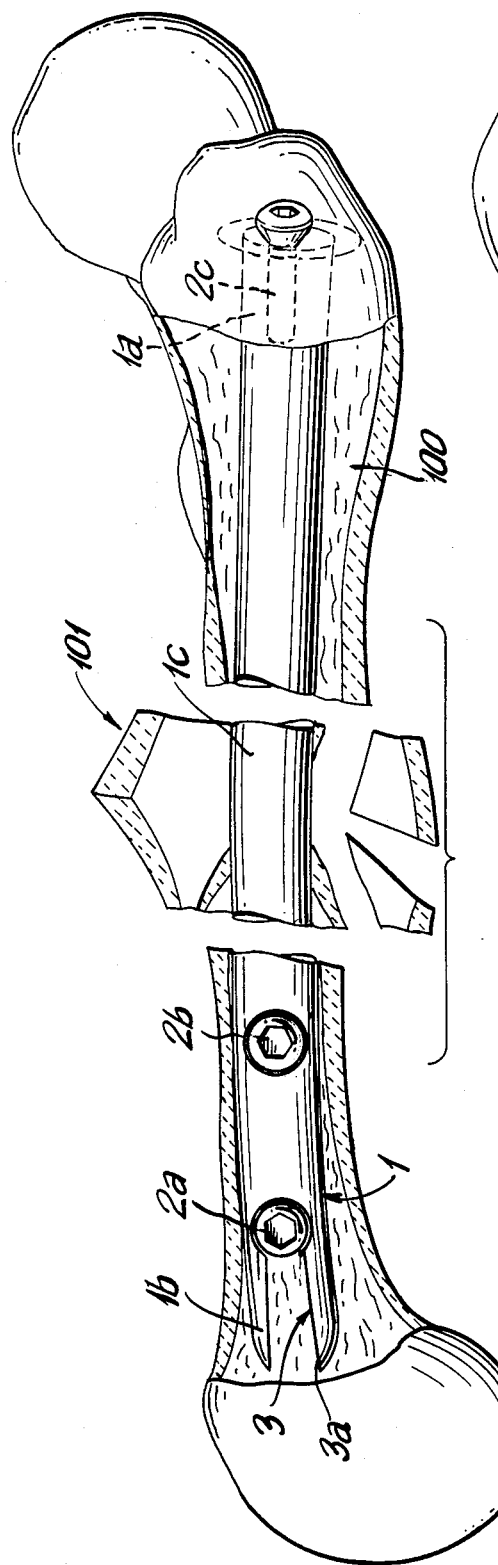
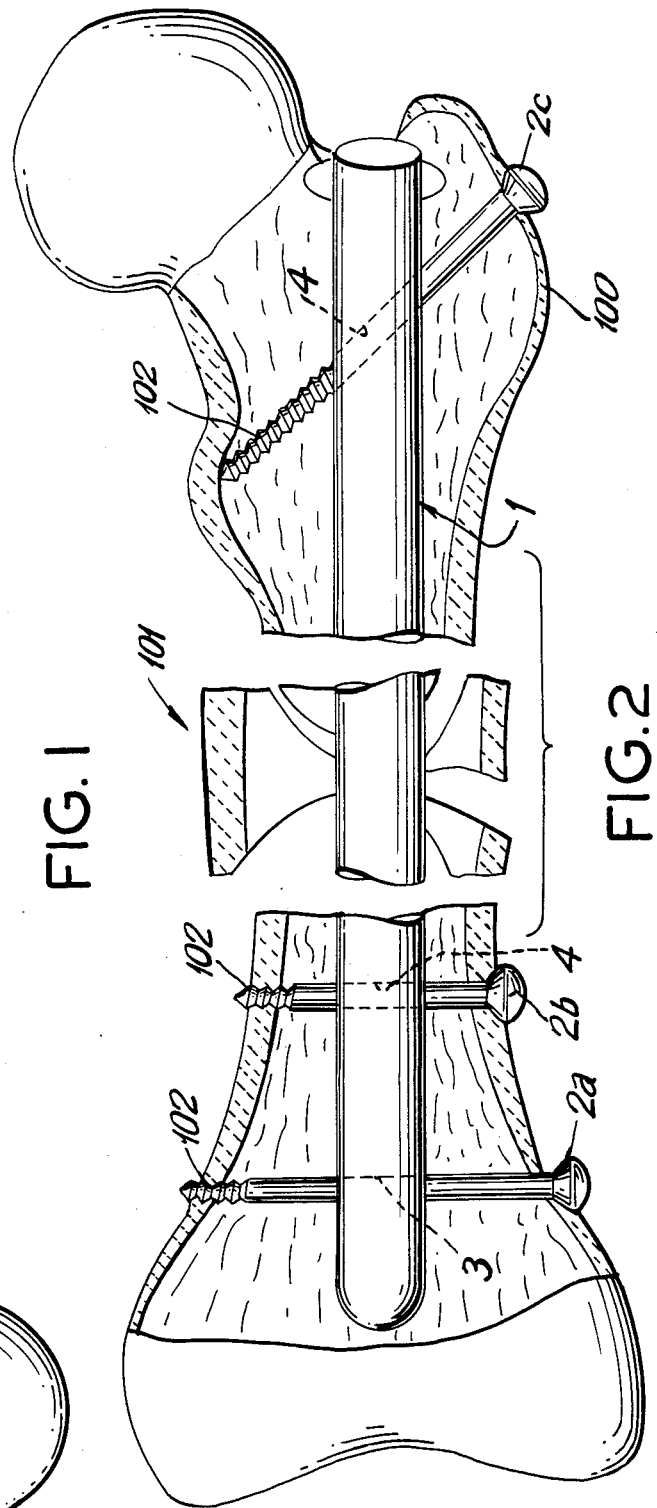

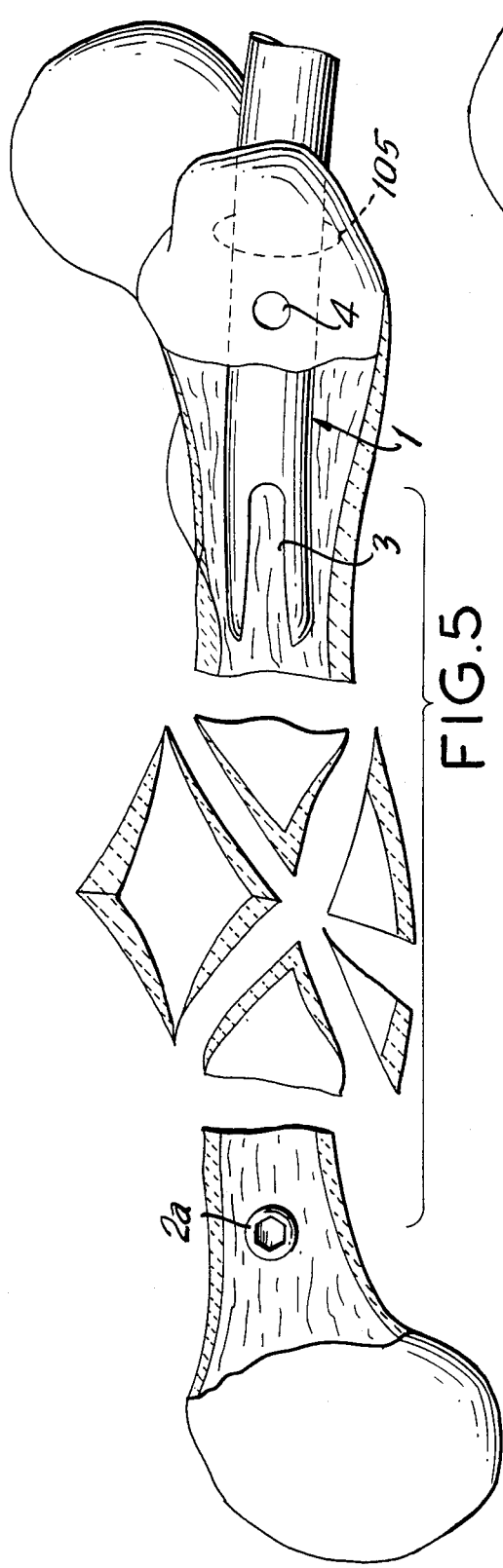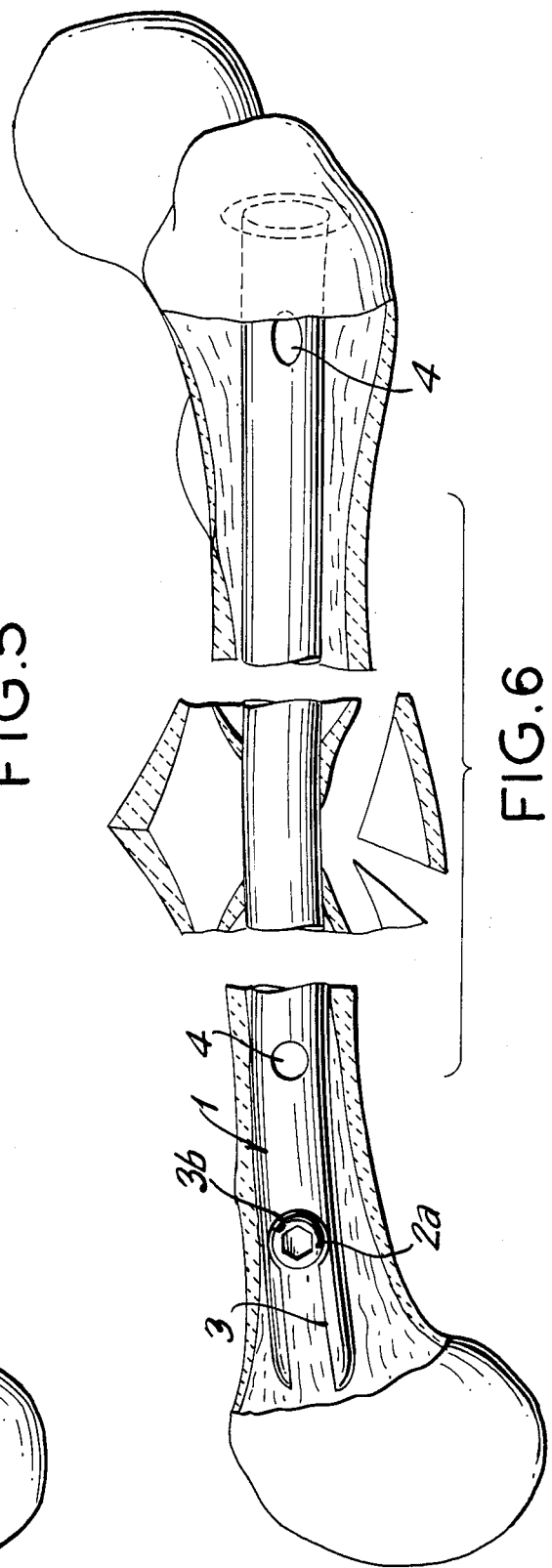

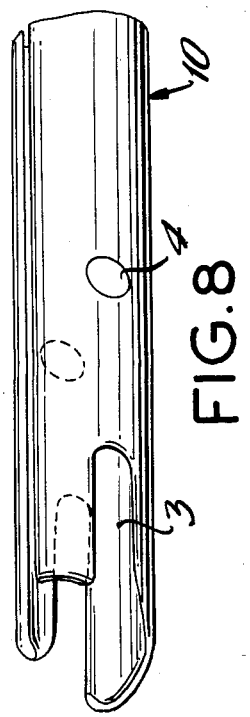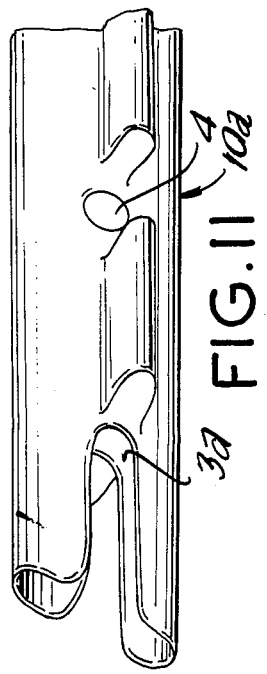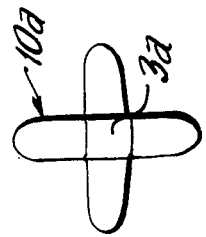
FIG.8　FIG.11　FIG.12
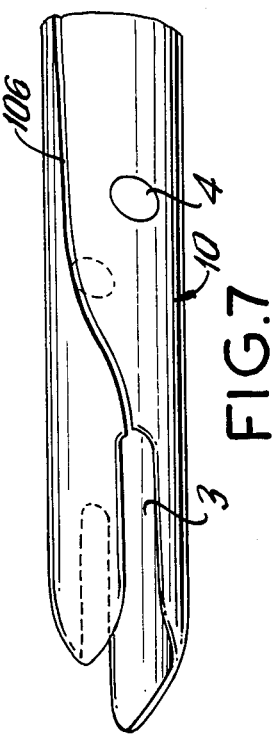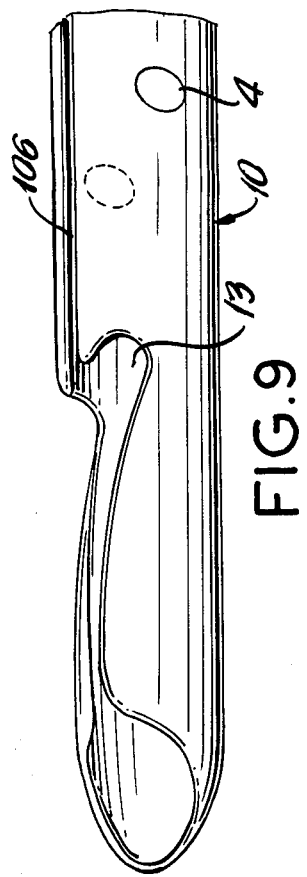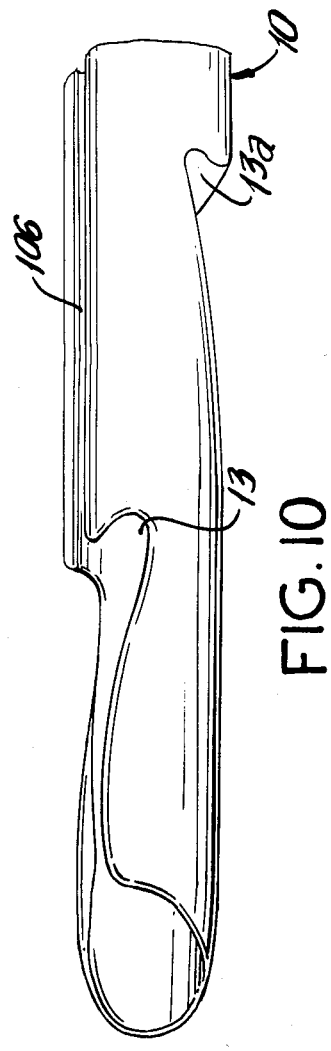
FIG.7　FIG.9　FIG.10

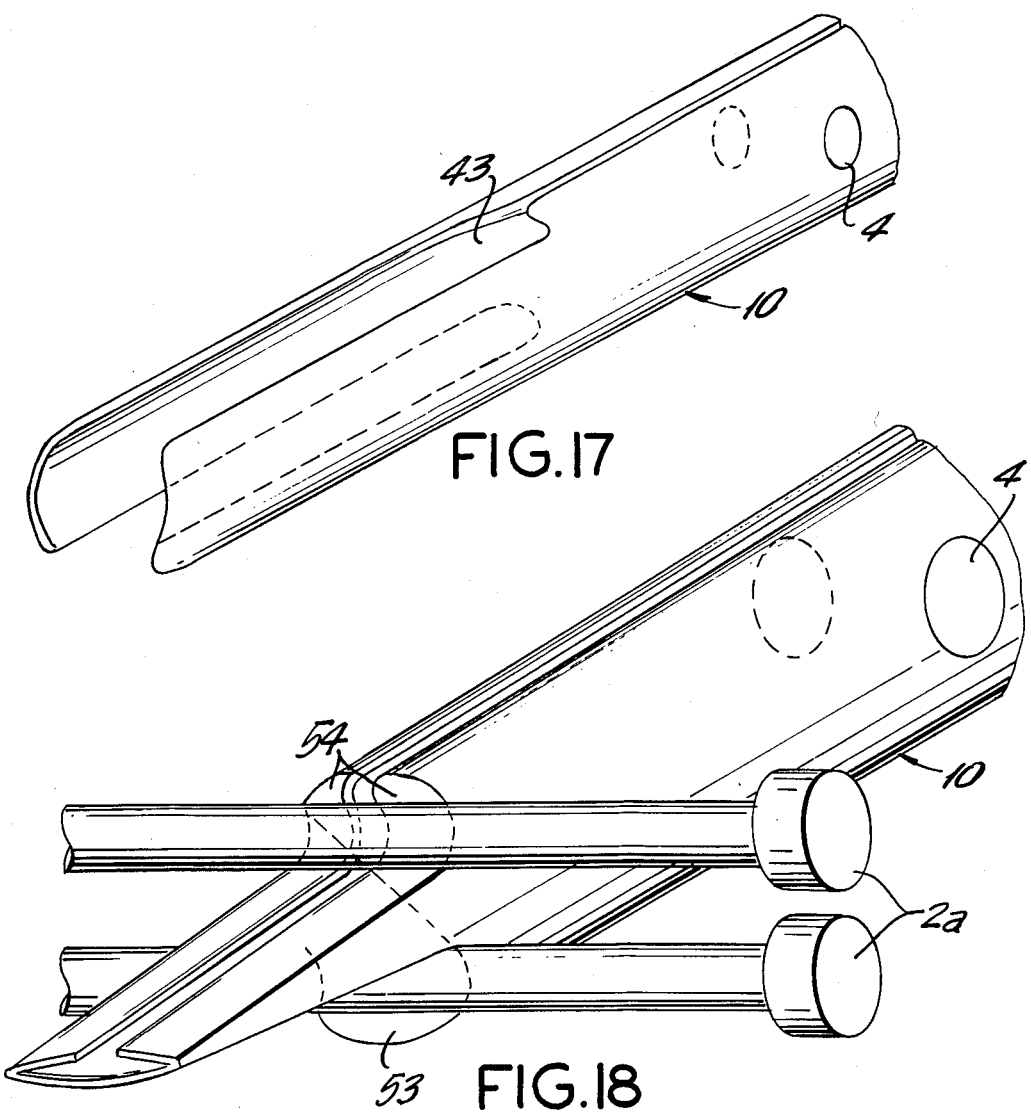
FIG.17
FIG.18
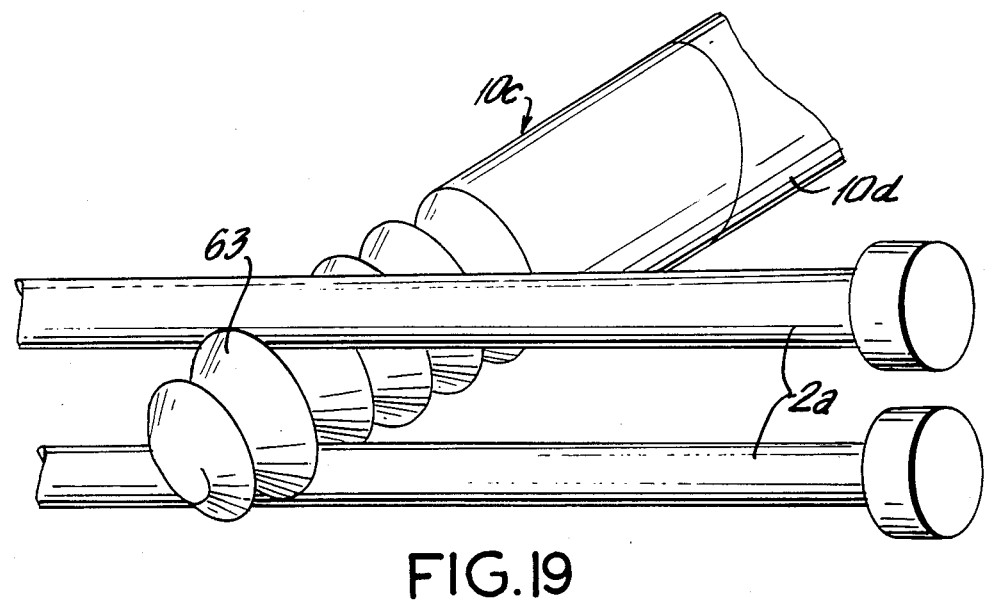
FIG.19

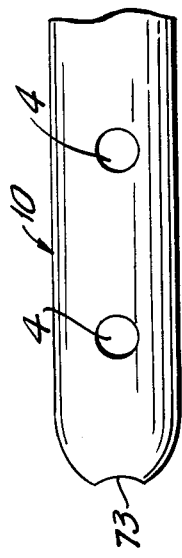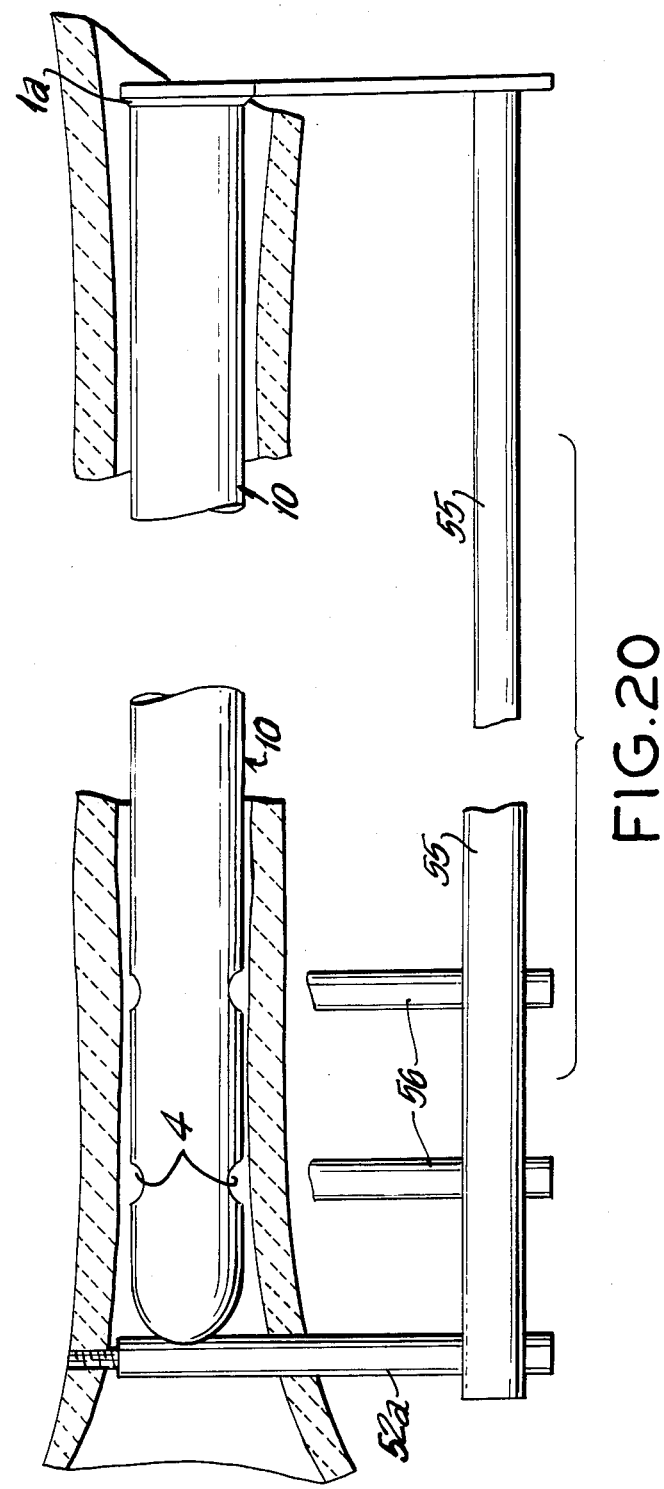
FIG. 21
FIG. 20

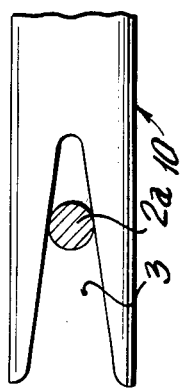 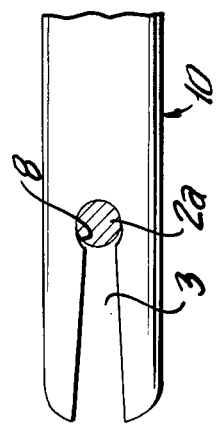 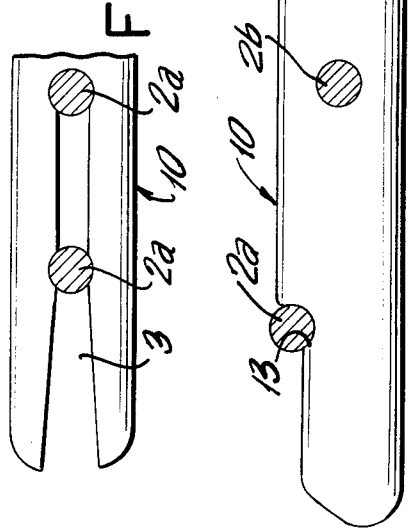 
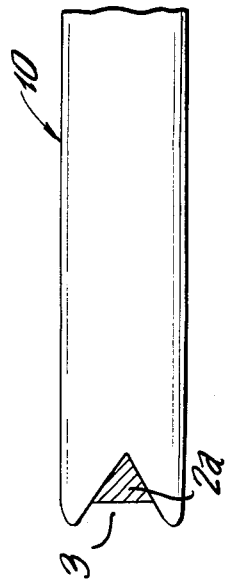 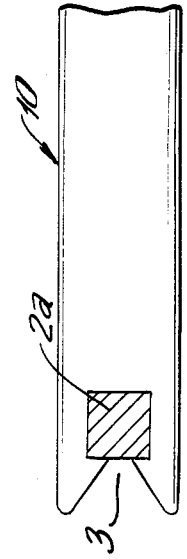 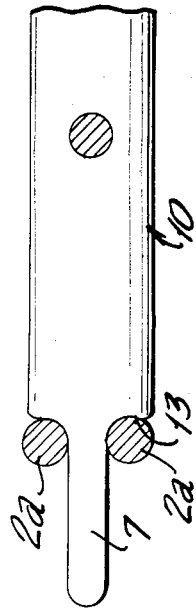 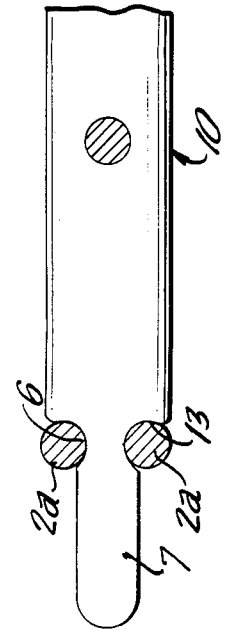

INTRAMEDULLARY NAIL

The present invention relates to intramedullary nails and nail assemblies and to a method for inserting intramedullary nails into bone medullae with increased safety and accuracy and with less pain and discomfort to the patient.

According to conventional practice, intramedullary nails are provided with holes through which securing bolts or pins are inserted transverse to the nail and the bone to secure the nail in the desired position. In the normal case, after the nail is inserted in the bone, a first securing bolt with a self-tapping thread is inserted through the bone and a transverse borehole in the nail near the tip of the nail. One or two additional bolts are thereafter inserted through holes near the head of the nail. With this procedure difficulties arise because the transverse securing bolts, including the first bolt, must meet the holes in the nail precisely. However, these holes are covered by soft tissue and the bone itself. To locate the boreholes, and specifically the hole for the first bolt precise, sighting mechanisms must be employed with constant use of radio-optic means with image amplification. This technique is not only complicated but can lead to undesirably high radiation dosage for the patient.

In accordance with the present invention, these difficulties are overcome by inserting a first bolt into the bone in a direction transverse to the bone medulla. An intramedullary nail having a tip with means adapted to engage the previously inserted bolt is then driven into the medulla until it engages the bolt. Since the positions of the other holes in the nail are known relative to the engaging means, other bolts can then be readily inserted.

The invention further includes a novel intramedullary nail having a shank with a head and a tip for insertion into the medulla of a bone, said nail having means adjacent said tip for engaging a bolt previously inserted into the bone with its axis generally transverse to the axis of the bone.

The invention further includes an intramedullary nail assembly comprising an intramedullary nail having a head and a tip for insertion into the medulla of a bone and a bolt for insertion into the bone transverse to the bone axis, the tip of the nail having means for engaging said bolt.

The invention will be further described with reference to the accompanying drawings in which:

FIG. 1 is a schematic view in side elevation and partly in section, of an intramedullary nail according to the invention, with three securing bolts, for setting a femoral fracture;

FIG. 2 is a schematic view of the device shown in FIG. 1 rotated 90°;

FIGS. 3 to 6 are schematic views analogous to FIG. 1 and showing the several stages of nail insertion according to the invention;

FIGS. 7 to 11 are schematic views in side elevation of various alternative forms of nails according to the invention;

FIG. 12 is an end view of the nail of FIG. 11;

FIGS. 13 to 19 are schematic views in side elevation of other embodiments of nails according to the invention;

FIG. 20 is a schematic view of still another embodiment of a nail according to the invention, showing the positioning of additional securing bolts;

FIG. 21 represents a side view of the tip portion of the nail of FIG. 20, rotated 90°; and FIGS. 22 to 29 are fragmentary views in side elevation showing additional embodiments of nails according to the invention.

Figure 3:
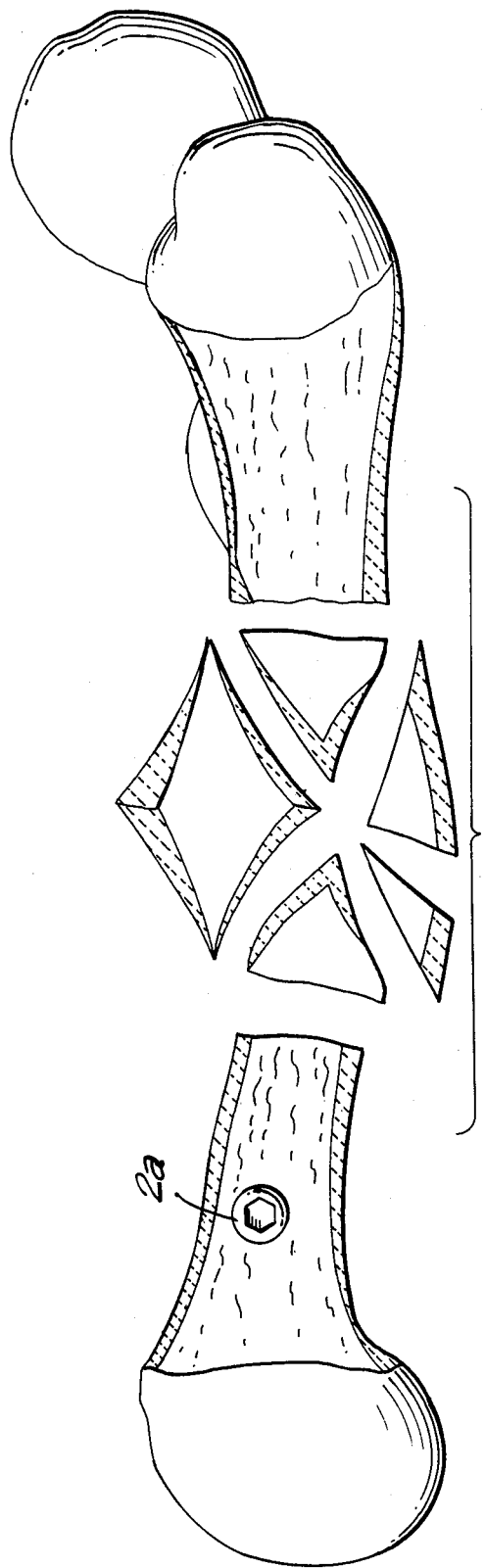

Referring to FIGS. 1 and 2, an intramedullary nail 1 comprising a hollow shank 1c having a head 1a and a tip 1b is shown inserted into a femur 100 having a fracture as at 101. The nail 1 is secured by three securing bolts 2a, 2b, 2c, each having self-tapping end threads 102. To engage the first bolt 2a, the tip of the nail 1 has a slot 3 whose width corresponds to the diameter of the central portion of bolt 2a. Conveniently the mouth 3a of the slot is somewhat expanded so that it is larger than the diameter of the bolt 2a. Transverse boreholes 4 are provided in the nail 1 for bolts 2b and 2c, either along a diameter of the nail or at an acute angle to the nail axis.

Figure 4:
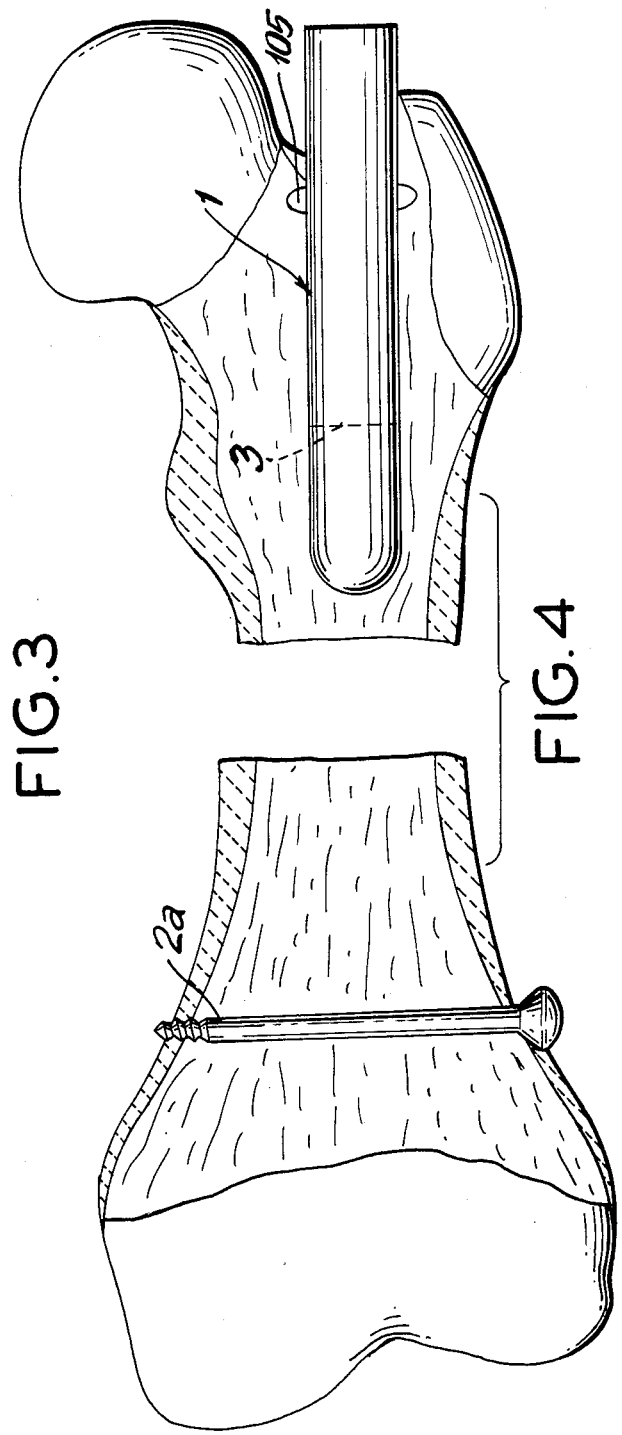

The positioning of the nail assembly shown in FIGS. 1 and 2 is illustrated in stages in FIGS. 3 to 6. After the usual preliminary work (repositioning, boring, etc.) bolt 2a, serving as the first bolt, is inserted in the bone at a predetermined location (FIG. 3). Subsequently, nail 1 is introduced through the proximal insert opening in the medulla bore 105 (FIGS. 4 and 5). The fish-mouth shaped slot 3 of the tip 1a of nail 1, having a relatively wide opening, engages the shaft of the bolt 2a until the bolt is seated in the rounded base 3b of the slot 3 (FIG. 6). Minor, often unavoidable deviations of the path of the nail as it is inserted with reference to the position of bolt 2a are compensated for during insertion of bolt 2a into slot 3 by the fact that the slot tapers towards the inside to the bolt diameter. With the nail 1 locked in its desired position by bolt 2a the axial and circumferential positions of boreholes 4 provided for additional bolts 2b and 2c can be determined precisely from outside the bone. Thus, precise monitoring of the individual steps is, as a practical matter, required only during the last phase of nail insertion and probing for the borehole for the first bolt, which is painful for the patient, becomes unnecessary.

In the foregoing description it has been assumed that bolt 2a, set before inserting the intramedullary nail, is also the first securing bolt. For the initial bolt, however, a so called target bolt can be used. This can then be removed after the correct engagement of the tip of the nail and replaced by a securing bolt.

The device as described in FIGS. 1 through 6, can be modified in various ways with reference to the design of the nail tip and the engaging portion of the bolt. A prerequisite, however, is that the nail can be engaged through its longitudinal displacement by a bolt transverse to and preferably at right angles to the nail axis. This necessarily leads to methods of application described above that are advantageous in terms of saving time and monitoring and avoiding the patient's suffering and discomfort.

Different variations of the nail and bolt structure according to the invention are represented in FIGS. 7 through 29. Thus, FIGS. 7 through 10 and 13, 14 show nail 10 formed in known manner as a cylindrical, longitudinally-slit (as at 106) tube. While in the embodiments of FIGS. 7, 8, 13 and 14, the tip portion of nail 10 has a slot 3, relatively wide at least on the insert side, and more or less axial, in the variations according to FIGS. 9 and 10, the tip of the nail is somewhat flattened on the side with the longitudinal slit 106 and is provided with a notch 13 cut open towards the tip of the nail. A transverse borehole 4 is provided in the embodiment of FIG. 9 for the insertion of an additional bolt analogous to the embodiments of FIGS. 1 through 8. In FIG. 10 the nail 10 has a second notch 13a, on the side of the nail opposite to the notch 13 and axially displaced from the notch 13. When using the variations shown in FIGS. 9 and 10, after setting the first bolt, the tip of the nail is run under this bolt until same is caught completely in notch 13.

FIGS. 11 and 12 show a nail 10a, having a cruciform profile. This is also provided with a slot 3a.

Figure 13:
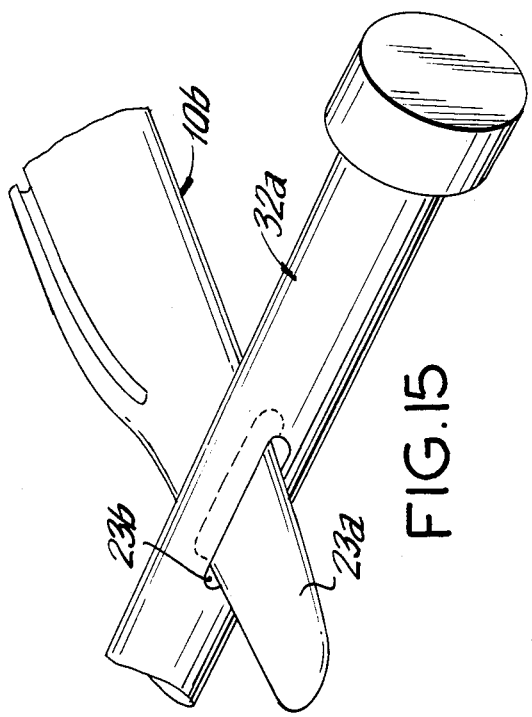
Figure 14:
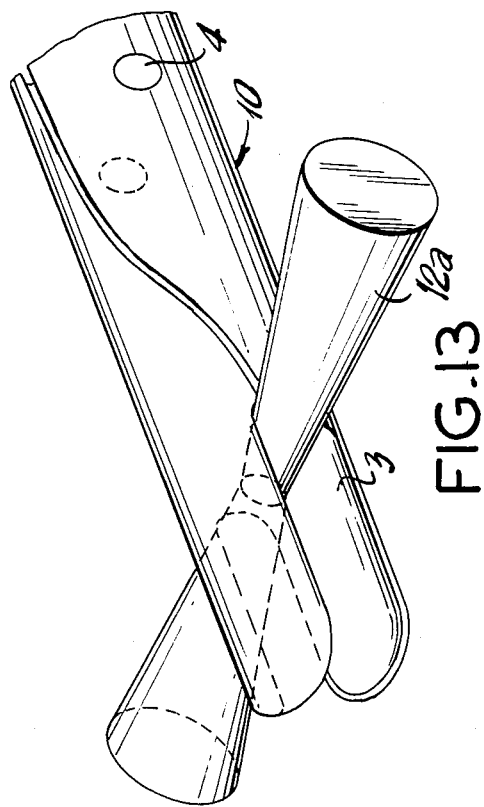

FIG. 13 illustrates the use of a bolt 12a, having a double cone configuration with the smallest cross-section in the middle. FIG. 14 shows a bolt 22a thickened in the middle. Both variations can be used for the first bolt in place of a cylindrical bolt. Both variations require a relatively large borehole, corresponding to the largest bolt diameter, but on the other hand, both shapes secure the nail against lateral shifts and thus effect a centering of the nail, when the nail is engaged with the bolt.

Figure 15:
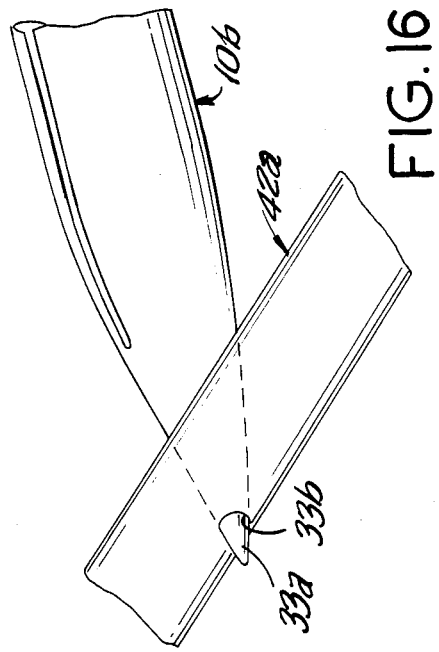
Figure 16:
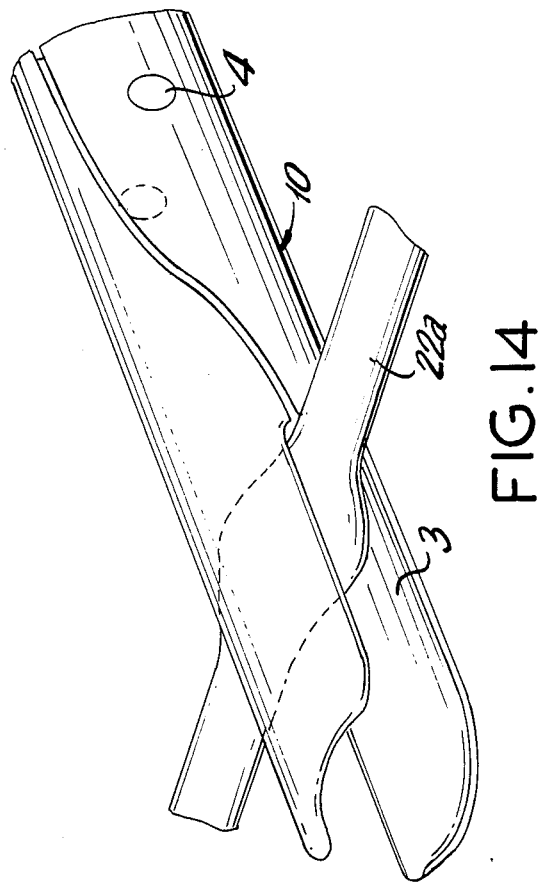

In all the embodiments of the invention described above the bolt has a shaft portion engaging a slot or groove in the tip of the nail. FIGS. 15 and 16 show, however, that the reverse is also possible. Thus, in the embodiment shown in FIG. 15, the shaft of first bolt 32a has longitudinal slot 23b into which is inserted a flattened tongue 23a, of the nail 10b, which nail is formed as a longitudinally slit tube. Analogously, in the embodiment according to FIG. 16, a conical transverse hole 33b is provided in the shaft of first bolt 42a, into which the tip 33a of nail 10b formed as a cone tapering to a point, is inserted. To increase the stability of the bolts, the shaft of the bolt 42a, which may be weakened by slot 23b or conical hole 33b, can be thickened.

The embodiments described above all presuppose that one or more additional securing bolts are inserted parallel to the axis of the first bolt. This, however, is in no way mandatory. As FIG. 17 shows, it is also possible to provide nail boreholes 4 for additional bolts at right angles to the plane of slot 43. In this case as well as in the other embodiments described above, the exact determination of the insert points or bore holes 4 for additional bolts is possible without great difficulty using a suitable measurement device, after fixing the first bolt in the slot of the nail tip.

In the embodiments described above, only one bolt is provided for the initial fixation of the nail. However, as the embodiments of FIGS. 18 and 19 show, two first bolts 2a can be inserted in the bone at a short distance from each other parallel to the axis of a plane at right angles to the medulla borehole. Pursuant to FIG. 18, the tip 53 of nail 10 is flattened to a wedge with rounded shoulders 54 shaped to the profile of bolts 2a. The pitch of bolts 2a, i.e., the distance between them, set before introduction of nail 10, is selected in such manner that when the nail is completely inserted, shoulders 54 abut the two bolts 2a. In contrast to the embodiment of FIG. 18, the tip portion of the cylindrical nail 10c shown in FIG. 19 is provided with thread portion 63, the core diameter of which corresponds to the pitch of bolts 2a so that it can be inserted solidly between the bolts 2a. The upper shaft portion 10d of nail 10c can be made detachable from the tip, so that after setting both bolts 2a, the separate threaded tip portion 63 can be inserted between the bolts and then the nail shaft 10d attached to the threaded portion 63.

A further embodiment is represented in FIGS. 20 and 21. The slightly beveled tip portion of nail 10 provided here has a transverse channel or groove 73 which is intended to engage a target bolt 52a set transversely to the medulla borehole before insertion of the nail. This target bolt is shown as threadless, though it may also be a normal bolt. While constantly measuring the depth of penetration, which is possible via a depth gauge of known design (not shown), the nail is driven in until it engages target bolt 52a with the groove 73; through slight turning of the nail, secure engagement of the target bolt 52a in the groove 73 can be assured. Tapered sleeves 56 for boring the bone openings for insertion of bolts in nail holes 4 can now be positioned exactly on telescoping pipe 55 fixed on the head 1a of the nail 10. After the introduction of the other bolts, target bolt 52a can be removed and replaced with a normal securing bolt, if desired.

It can be seen from the above, that numerous variations in the invention are possible, both with reference to the formation and arrangement of the engaging means provided on the intramedullary nail, and with reference to the type, number and position of the bolts to be set prior to introduction of the nail. In FIGS. 22 through 29, some other variants are illustrated.

In FIG. 22 the slot 3 in the tip of the nail 10 is V-shaped and the bolt 2a is held midway down the slot. In FIG. 23 a socket 8 is provided at the end of a tapered slot 3. In FIG. 24, two bolts 2a are lodged in the same slot 3, one behind the other. In FIG. 25 the bolt 2a lodges in a notch 13 formed on one surface of the nail 10.

FIGS. 26 and 27 show bolts 2a of polyhedral crossection. In FIG. 26 the bolt 2a is triangular; in FIG. 27 it is square. In FIGS. 28 and 29 two bolts 2a, in a plane transverse to the nail axis are used, the nail having a tongue 7 which is engaged between them. In FIG. 29 grooves 6 are provided at the base of the tongue to receive the bolts 2a.

The one common feature among the foregoing embodiments is that a positive connection of the nail and the first bolt is possible without location problems, since the nail, movable axially in the medulla borehole necessarily engages the first bolt. After this first engagement the precise position of the other boreholes corresponding to the additional bolts can be determined from the outside without difficulty. The individual elements of the device, i.e., the nail and the securing bolts, are no more complicated than those of known devices, but make possible a far more rapid and considerably less painful operation.

What is claimed is:

1. An intramedullary buttressing nail for stabilizing the position of bone fragments subsequent to the reduction of a bone fracture, said nail having a shank with a head and a tip for insertion into the medulla of a bone along the long axis of the bone, a slot adjacent the tip of the nail for slidingly engaging within said slot a bolt, previously inserted into the bone in a direction transverse to the axis of the bone, on the distal side of the fracture, as said nail is linearly advanced along the bone axis, said slot having a back wall which said bolt is adapted to abut when seated in the slot, thus limiting travel of the distal fragment of the bone in the proximal direction to avoid shortening of the bone during healing; said means in said nail for receiving a second fastener means for fixing said shank relative to said medulla.

2. The nail claimed in claim 1 wherein the means for receiving a second fastening means is a transverse recess in the shank of the nail between said slot and the head of the nail.

3. An intrameduallary buttressing nail assembly for stabilizing bone fragments subsequent to reduction of a bone fracture comprising an intramedullary nail and a first bolt, said nail having a shank with a head and a tip for insertion into the medulla of a bone along the long axis of the bone, a slot adjacent the tip of the nail for slidingly engaging within said slot, as said nail is linearly advanced along the bone axis, said first bolt previously inserted into the bone in a direction transverse to the axis of the bone on the distal side of the fracture, said slot haing a back wall which said first bolt is adapted to abut when seated in said slot, thus limiting travel of the distal fragment of the bone in the proximal direction to avoid shortening of the bone during healing; and means in said nail for receiving a second bolt for fixing said shank relative to said medulla.

4. The assembly claimed in claim 3 wherein the nail is provided with a recess for engaging said first bolt.

5. The assembly claimed in claim 3 wherein the tip of the nail has a reduced section and the bolt has a recess for receiving said reduced section.

6. The assembly claimed in claim 5 wherein the portion of the bolt containing said recess is thicker than other portions of the bolt.

7. The assembly claimed in claim 3 and comprising two securing bolts for insertion into a bone transverse to the medulla, the tip of said nail having a reduced portion for insertion between said bolts, this reduced portion being provided with shoulders interlocking with the bolts.

8. The assembly claimed in claim 3 wherein the bolt is threaded at one end.

9. The assembly claimed in claim 3 wherein said first bolt has, at least in part, a round cross-section.

10. The assembly claimed in claim 3 wherein said first bolt has, at least in part, a polyhedral cross-section.

11. A method of securing an intramedullary buttressing nail in the medulla of a fractured bone subsequent to reduction of the fracture which comprises inserting a first bolt into the bone transverse to the axis of the medulla on the distal side of the fracture and then inserting an intramedullary nail into the medulla along the long axis of the bone, said nail having a shank with a head and a tip, a slot adjacent the tip and a transverse recess between the slot and the head, said slot having a back wall, and said nail being inserted into said medulla so that said first nail slidingly engages the slot and is brought to abut said back wall when seated in the slot, thus to limit travel of the distal fragment of the bone in the proximal direction to avoid bone shortening during healing; andd subsequently inserting a second bolt transversely through said transverse recess to fix the shank of the nail relative to said medulla.

12. The method claimed in claim 11 wherein said first bolt is a temporary target bolt and comprising the step of replacing said target bolt with a securing bolt.

* * * * *